United States Patent
Winchell et al.

[11] 3,957,033
[45] May 18, 1976

[54] VENTILATION STUDY SYSTEM

[75] Inventors: Harry S. Winchell, Lafayette; Thomas C. Hall, Fremont, both of Calif.

[73] Assignees: General Electric Company; Medi-Physics, Inc., both of San Jose, Calif.

[22] Filed: Aug. 15, 1973

[21] Appl. No.: 388,489

[52] U.S. Cl. ............ 128/1.1; 128/2 A; 128/2.08; 128/184; 128/202; 250/506; 251/292

[51] Int. Cl.² .......................... A61B 6/00

[58] Field of Search ........... 128/2 A, 1.1, 184, 2.08, 128/202; 250/506; 251/292, 368

[56] References Cited
UNITED STATES PATENTS

| | | | |
|---|---|---|---|
| 662,658 | 11/1900 | Sterne | 128/184 |
| 818,123 | 4/1906 | Rousseau | 128/202 |
| 827,910 | 8/1906 | Hollenberger | 128/202 |
| 1,830,453 | 11/1931 | Wassmer | 128/184 |
| 3,088,456 | 5/1963 | Stanton | 128/202 |
| 3,369,121 | 2/1968 | Bruno et al. | 250/506 |
| 3,409,776 | 11/1968 | Pipher et al. | 128/1.2 X |
| 3,438,365 | 4/1969 | Packer et al. | 128/1.2 |
| 3,666,955 | 5/1972 | Suprenant et al. | 128/2.08 X |
| 3,695,254 | 10/1972 | Blum | 128/1.1 X |
| 3,769,967 | 11/1973 | Jones et al. | 128/2.08 |

*Primary Examiner*—Kyle L. Howell
*Attorney, Agent, or Firm*—Ivor J. James, Jr.; Sam E. Laub; Samuel E. Turner

[57] ABSTRACT

A disposable ventilation study system for dispensing a single-patient dosage of gaseous radioisotopes to patients for pulmonary function studies is disclosed. A gas impermeable capsule encloses the gaseous radioisotope and is stored within a radioactivity shielding body of valve means which shears the capsule to dispense the radioisotope to the patient. A breathing bag receives the patient's exhalation of the radioisotope and permits rebreathing of the radioisotope by the patient.

12 Claims, 7 Drawing Figures

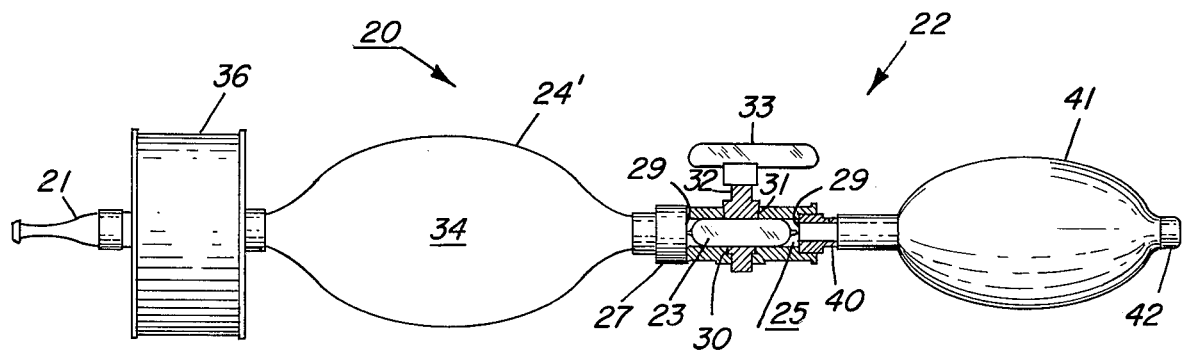
Fig. 5
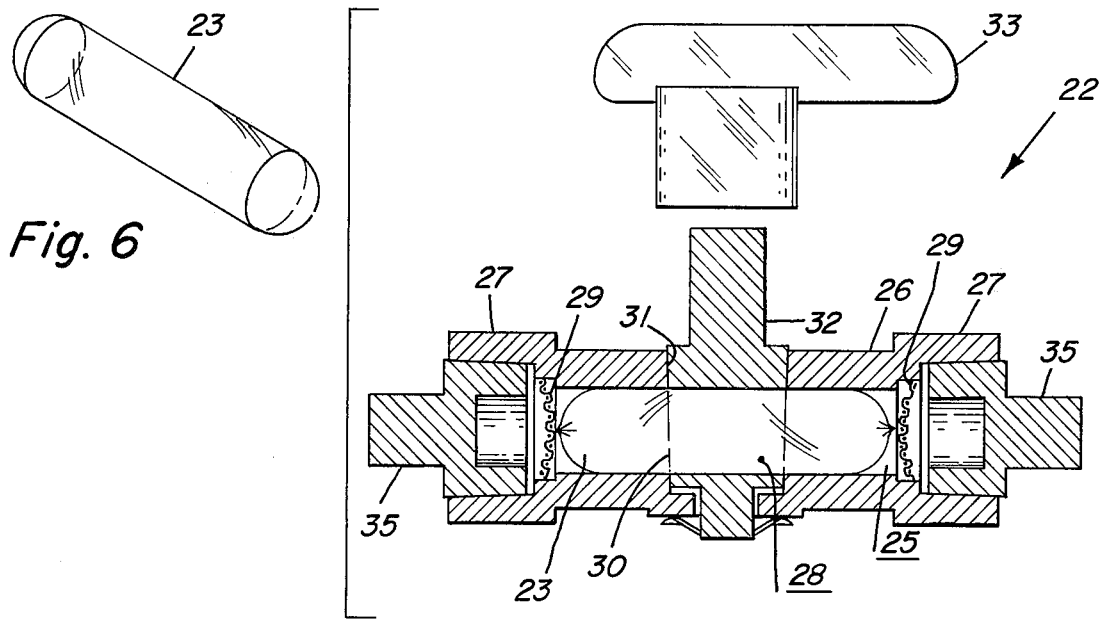
Fig. 6
Fig. 7

VENTILATION STUDY SYSTEM

BACKGROUND OF THE INVENTION

This invention relates to an apparatus for dispensing single doses of gaseous radioisotopes to a patient.

Radioactive isotopes of xenon and other radioisotopes are useful in the field of medicine and particularly in medical diagnosis. There is increasing use of xenon-133 in the medical field for studying blood flow in muscles, scanning the lungs for lung functional disorders (e.g., emphysema and emboli), scanning the brain and scanning for cardiac abnormalities. For scanning of the lungs, xenon-133 can be introduced into a human body by one of two processes. In an inhalation process, the patient breathes a gas containing xenon-133 and the xenon-133 is drawn directly into the patient's lungs. In an injection process, a saline solution containing dissolved xenon-133 is injected into the blood stream of the patient and through perfusion the xenon-133 goes to various organs of the patient, including the patient's lungs. Radioactive gases having more optimum imaging characteristics for specific purposes may also be used, such as xenon-127.

One current practice of formulating a xenon-133 solution for medical applications is to dissolve the xenon-133 directly into a saline solution to achieve gas concentrations appreciably below saturation of the xenon-133 in the solution at the temperature of dissolution. This avoids any occurrence of bubble formation in the solution during use. In further detail, the present procedure used in the medical profession for preparing injectable doses of xenon-133 as an aqueous solution involves crushing an ampoule containing xenon-133 in a container filled with a normal saline solution.

The difficulties in handling and storage of xenon and in particular of a radiopharmaceutical xenon-133 solution are set forth in the Journal of Nuclear Medicine in Volume 11 at page 352 (1970) and Volume 13 at page 231 (1972). These difficulties can be summarized as follows: (a) there is loss of xenon-133 into air spaces resulting as individual doses are removed from multidose vials since it is difficult to prevent the introduction of air bubbles when replacing the volume withdrawn from the vial; (b) there is diffusion of xenon-133 into rubber components in contact with the xenon-133 such as in elastomeric systems at the end of cylindrical glass capsules and rubber septums on multidose vials; and (c) there is diffusion of xenon-133 into both the plastic and rubber components of disposable syringes used for injection of the patient.

Studies have been made regarding the trapping of radioactive xenon in various materials, and these studies show that elastomers and a variety of materials will take up significant quantities of radioactive xenon. As a result of these studies, only glass syringes, which take up less than 1% of the xenon-133 from the solution, are used for dispensing such radioactive xenon solutions. However it has remained desirable to minimize the foregoing difficulties and to further reduce the loss of radioactive xenon isotopes to the materials used to package doses of the radioactive xenon isotopes.

The widest use of xenon-133 is in pulmonary function studies and this involves having the patient inhale a dose of gaseous xenon-133, and while the patient holds his breath a scintillation camera is used to take a picture of the patient's lungs. This picture shows any portions of the patient's lungs not functioning or not properly functioning.

The use of xenon-133 in pulmonary function studies has required quantities of xenon in patient dosage sizes accurately measured and readily administered to the patient. There have been several devices designed for holding and administering dosage sized quantities of gaseous radioactive xenon to patients, and design of such devices has attempted to meet the following requirements, namely ease and safety in administration to the patient; effective radiation shielding during shipment, storage and handling incidental to administration to the patient; a container insuring substantial retention of the radioactive xenon prior to administration to the patient; a container suitable for re-collection of the radioactive xenon after administration to the patient; a system capable of providing multiple administrations to the patient; absence of absorption of the radioactive xenon by the materials holding the dosage size quantity of radioactive xenon; and a dispensing device providing a high concentration of xenon in one inhalation.

One device for holding and administering dosage sized quantities of gaseous radioactive xenon is a Calidose gas dispenser shown in FIG. 1. This dispenser unit 10 is loaded with a glass vial 11 closed off with an elastomeric septum 12 and the glass vial 11 holds the gaseous xenon prior to administration to a patient. The dispenser unit 10 has a manually operated plunger 13 for pushing the septum 12 in the glass vial 11 against two hollow needles 14 and 15 for puncturing the septum 12. A manually operated rubber squeeze bulb 16 is connected to one hollow needle 15 and flushes the xenon from the glass vial 11 through the other hollow needle 14 into a nozzle 17 and into a breathing apparatus (not shown) held in the patient's mouth.

Another device for discharging quantities of gaseous radioactive xenon is shown and described in Volume 92 of Radiology at pages 396-7 (February, 1969). A gas cylinder containing radioactive xenon is filled with carbon dioxide to a pressure of 3 atmospheres giving a xenon-carbon dioxide mixture in the cylinder. A small quantity of the mixture is withdrawn from the cylinder through a micrometer needle valve. The amount of xenon-133 dispensed can be measured by placing the syringe inside a calibrated well-type ionization chamber. Radioactive xenon gas which is to be used in a closed-circuit spirometer system can be taken up into a Hamilton gas-tight syringe for transfer.

Another procedure is to use a hypodermic syringe to inject air into an ampoule sealed by a septum containing radioactive xenon and then to withdraw a fraction of the air-xenon mixture. The syringe is exhausted into a closed-circuit spirometer and the patient breathes the gases in the closed-circuit spirometer. This also has the septum absorbing a portion of the radioactive xenon.

Accordingly it has remained desirable to have a xenon dosage dispensing apparatus for patients providing a patient sized dose of radioactive xenon.

Summary of the Invention

The ventilation study system of this invention has (1) an internal, gas-retaining volume (2) a shearable capsule containing a gaseous radioisotope, (3) a valve means holding the capsule within an interior cavity thereof which forms a portion of the gas-retaining volume of the system, shielding the radioactivity emitted from the radioisotope and capable of shearing the capsule to release the gaseous radioisotope into the gas-retaining volume defined by the system, (4) patient breathing means in communication with the internal cavity of the valve means and (5) a breathing bag defining a portion of the gas-retaining volume of the system and in communication with the internal cavity of the valve means.

The shearable capsule has a gas impermeable enclosure holding the gaseous radioisotope which in one preferred embodiment is xenon.

The valve means has (1) a shielding valve body defining an internal cavity for enclosing a capsule and a bore intersecting the cavity intermediate the ends of the cavity and at an intermediate point of the capsule when the capsule is inserted in the internal cavity, and (2) a valve plug within the bore having a valve opening concentric and normally aligned with the interior cavity. Detachable handle means is provided for rotating the valve plug to shear the capsule at the intersection of surfaces defining the interior cavity and valve opening.

The ventilation system can include, in addition, means capable of absorbing gases such as carbon dioxide and water vapor where the system is to be used for repeated inhalations by the same patient.

Accordingly it is an object of this invention to provide a disposable ventilation study system for conducting pulmonary function studies using a gaseous radioisotope.

Another object of this invention is to provide a disposable ventilation study system enabling multiple inhalations by a patient for pulmonary function studies.

Still another object of this invention is to provide a ventilation system for conducting pulmonary function studies having a gas impermeable enclosure to avoid loss of the radioisotope by diffusion during storage, shipment, patient administration and disposal following use.

A further object is to provide a ventilation study system having a valve means shielding the radioactivity of the radioisotope and capable of dispensing the radioisotope for use.

Other objects and advantages of this invention will become apparent to the person having ordinary skill in the art from reading the following specification, the appended claims and by reference to the drawings described immediately below.

DESCRIPTION OF THE DRAWINGS

FIG. 5 presents a partial sectional view of the ventilation study system of FIG. 4 having an additional element of an absorbing means.

FIG. 6 presents an isometric view of the capsule enclosed within the valve means of FIGS. 2–5.

FIG. 7 presents a sectional view of the valve means used in the ventilation system of FIGS. 2–5 having in addition end plugs inserted in each opening to give a unit suitable for shipment.

DESCRIPTION OF THE INVENTION

Figure 1:
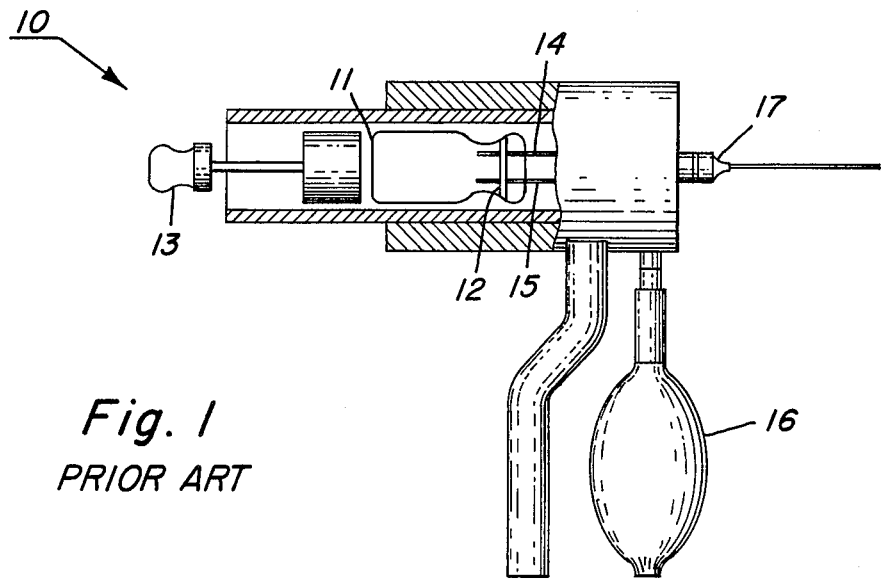
FIG. 1 presents a partial sectional view of a device for holding and administering dosage sized quantities of gaseous radioactive xenon according to the prior art as described above under Background of the Invention.
Figure 2:
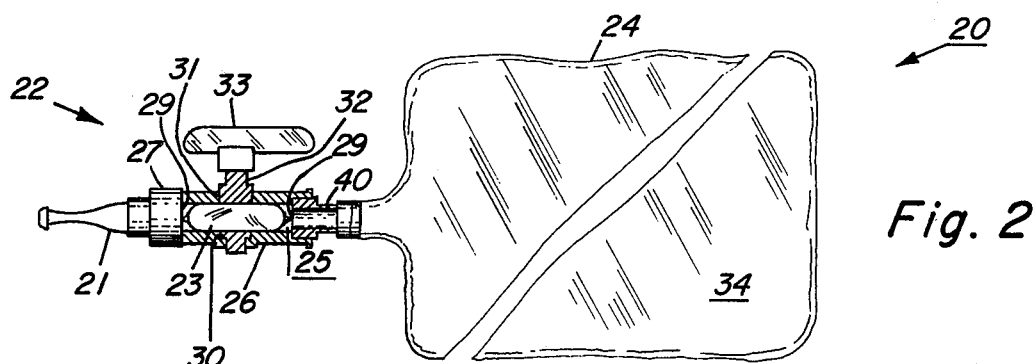
FIG. 2 presents a partial sectional view of one embodiment of the ventilation study system of this invention having valve means interposed between the breathing means and the breathing bag.

Referring now to FIG. 2 there is shown a ventilation study system according to the teaching of this invention generally designated as 20 and generally comprised of patient breathing means 21, here in the form of a mouthpiece, a valve means 22 holding and capable of shearing the capsule 23 and a breathing bag 24. The ventilation study system 20 has an internal gas-retaining volume defined by the breathing bag 24 and the valve assembly 22 with the breathing means 21 representing an outlet to the volume. The breathing means 21 is a hollow generally cylindrical tube such as a tube comprised of injection molded polyethylene with one end generally flattened to a mouthpiece designed to fit into a patient's mouth. The breathing means 21 is connected to one end of the valve body 26 of valve means 22 in an air tight seal so that the breathing means is in communication with an internal cavity 25 of the valve means in which is positioned a shearable capsule 23 described more fully below in reference to FIG. 6. The internal cavity 25 forms a portion of the internal gas and irradiation retaining volume of the ventilation study system 20.

The valve means 22 will now be described in greater detail with reference to FIG. 7 in addition to FIG. 2. The valve means 22 has a shielding valve body 26 of generally cylindrical cross section with expanded ends 27 and defining an interior cavity 25 for holding and generally enclosing capsule 23 in a manner shielding any radiation emitted from the capsule 23. The expanded ends 27 have screens 29 which are gas-transmitting, particle-retaining screens provided to insure that any particulate material generated in the ventilation system 20, such as from shearing of capsule 23, is retained in the system 20. Valve body 26 has a bore 31 intersecting the cavity 25 at a position intermediate the ends of the cavity 25 and generally intermediate to the position of the capsule 23 with valve plug 30 being positioned within the bore 31. The valve plug 30 has an opening 28 concentric with the interior cavity 25 and the opening 28 is normally aligned with the internal cavity 25. The valve plug 30 has a stem 32 fitting a handle 33 for rotating the plug 30 to provide a shearing action at the intersection of the surfaces defining the interior cavity 25 and the opening 28 of the valve plug 30 to shear the capsule 23 into three pieces and release the radioisotope from the capsule 23.

FIG. 7 shows a unit comprising a package suitable for shipment having end plugs 35 inserted in each opening in the expanded ends 27 of valve means 22. This package holds the capsule 23 which encapsulates the radioisotope and the package forms a gas-tight and radiation-tight container. The handle 33 is detached from the unit during shipment. The container consists of end plugs 35, valve body 26 and valve plug 30.

The valve means can be made of a variety of materials with representative materials including a lead alloy such as a lead alloy having about 5% by weight tin, about 11% by weight antimony and the balance is lead.

Again referring to FIG. 2, a breathing bag 24 is connected to the insert 40 fitting the other end of valve means 22 in an air tight seal so that the cavity 34 defined by the breathing bag is in communication with the interior cavity 25 of the valve means 22. The cavity 34 of the breathing bag 24 forms a portion of the internal gas retaining volume of the ventilation system.

Figure 3:
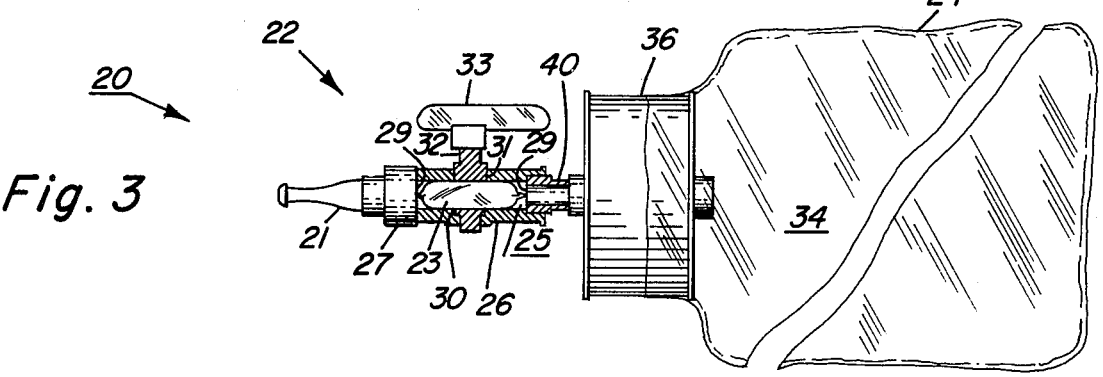
FIG. 3 presents a partial sectional view of the ventilation study system of FIG. 2 having an additional element of an absorbing means.

Another embodiment of the ventilation study system of FIG. 2 is presented in FIG. 3 with the same elements having identical numbering as in FIG. 2. An absorbing means 36 in the form of a cannister of absorbing material is interposed between the breathing bag 24 and the valve means 22 in an air tight connection. The cannister holds a chemical such as Baralyme for chemically combining with carbon dioxide and water vapor in the breath being exhaled by the patient. This embodiment has the advantage that it can be repeatedly used by the patient where the pulmonary function study is designed for repeated inhalation by the patient. The cannister enables absorption of the carbon dioxide and water-vapor in the exhalation of the patient so that the patient does not build up carbon dioxide during repeated inhalation. The breathing bag 24 is sealed to the absorbing means 36 to give an air tight seal.

Figure 4:
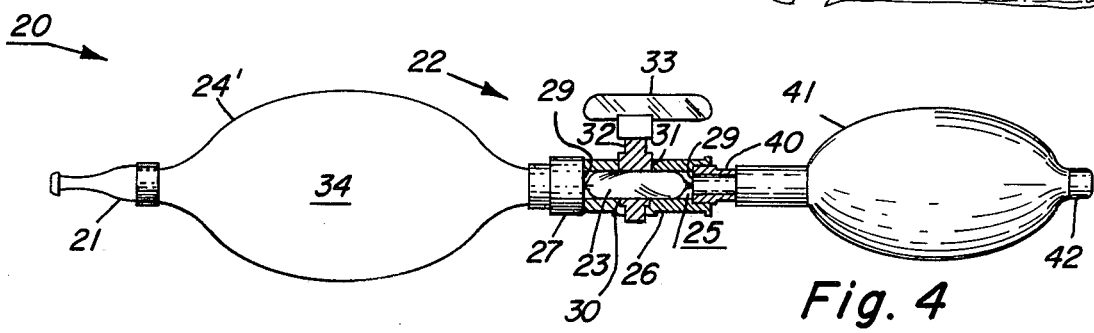
FIG. 4 presents a partial sectional view of another embodiment of the ventilation study system of this invention having the breathing bag interposed between the breathing means and the valve means.

Another embodiment of the ventilation system of this invention is presented in FIG. 4 with the same elements having identical numbering as in FIGS. 2 and 3. In this embodiment, the breathing means 21 is connected to one opening of a breathing bag 24' and valve means 22 is connected to another opening in breathing bag 24'. Insert 40 leading to cavity 25 of valve body 26 is connected to a rubber bulb expressor 41 for discharging the contents of the capsule 23 into the rest of the gas-retaining volume of the ventilation study system. Expressor 41 has a one-way valve 42 which emits air into the gas-retaining volume of the ventilation study system but does not enable any of the gas in the system to leave the system.

Another embodiment of the ventilation system of FIG. 4 is presented in FIG. 5 with the same elements having identical numbering as above. An absorbing means 36 in the form of a cannister is interposed between the breathing means 21 and the breathing bag 24' in an air-tight connection.

The capsule 23 shown in FIG. 6 is comprised of a shearable gas impermeable enclosure which contains a gaseous radioisotope useful for medical applications. Various materials meet the gas impermeable requirement of this invention and are capable of being readily sheared to release the gas with representative materials including polyethylene-terephthalate, vinyl-vinylidene chloride and polysulfone.

Various gaseous radioisotopes can be used in the practice of this invention and are sealed in the enclosure of capsule 23. A preferred radioisotope is a xenon-radioisotope including xenon-127, xenon-133, and xenon-129m. Other gaseous radioisotopes can be used including radon-222 and krypton-85. The person skilled in the art will realize that various gaseous radioisotopes can be selected and used depending upon the particular medical application at hand. One preferred configuration of the capsule 23 is shown in FIG. 6 generally in the form of a right cylinder with rounded ends.

For certain medical applications it may be desirable to include a diluent with the gaseous radioisotope in the capsule 23. Representative diluents are air, nitrogen, medical grade air or oxygen. Moisture or water vapor or other physiologically benign absorbents for radiolysis products of the capsule enclosure material also may be added.

The ventilation study system of this invention offers many advantages for dispensing dosage size quantities of a gaseous radioisotope to patients. Among these advantages are ease and safety in administration to the patient, effective radiation shielding during shipment, storage and handling incidental to administration to the patient, a container insuring substantial retention of the radioactive xenon prior to administration to the patient, a container suitable for re-collection of the radioactive xenon after administration to the patient, a system capable of providing multiple administrations to the patient, absence of absorption of the radioisotope by the materials holding the dosage size quantity of the radioisotope and a system providing a high concentration of radioisotope in one inhalation.

As will be apparent to those skilled in the art, various modifications and changes may be made in the invention described herein. It is accordingly the intention that the invention be construed in the broadest manner within the spirit and scope as set forth in the accompanying claims.

What is claimed is:

1. A ventilation study system for pulmonary function studies in patients, said system having an internal, gas-retaining volume comprising:
   a. a shearable polymeric capsule containing a gaseous radioisotope;
   b. valve means comprised of a radiation shielding material having an internal cavity holding said capsule therein, with said cavity forming a portion of the gas-retaining volume of the system and said valve means further having a bore intersecting the cavity at an intermediate point of said capsule;
   c. a rotatable valve plug comprised of a radiation shielding material positioned within the bore and having an opening concentric and normally aligned with the internal cavity of said valve means, said valve plug causing, upon rotation thereof, said capsule in the internal cavity of said valve means to be sheared and thereby releasing said gaseous radioisotope;
   d. patient breathing means being operatively connected to the internal cavity of said valve means; and
   e. breathing bag means defining a predetermined portion of the gas-retaining volume of the system being operatively connected to said valve means so as to be in communication with the internal cavity thereof, said breathing bag means being adapted to receive the patient's exhalation containing said gaseous radioisotope.

2. A ventilation study system according to claim 1 in which the radioisotope is a xenon radioisotope.

3. A ventilation study system according to claim 1 in which said breathing bag means is comprised of polyethylene.

4. A ventilation study system according to claim 1 in which the valve means is comprised of a lead alloy.

5. A ventilation study system according to claim 4 in which the lead alloy is comprised of about 5% by weight tin, about 11% by weight antimony and the balance is lead.

6. A ventilation study system according to claim 1 further including absorbing means as part of the gas-retaining volume.

7. A ventilation study system according to claim 6 in which the absorbing means is connected to an opening of the valve means and said first means is connected to the absorbing means.

8. A ventilation study system according to claim 1 wherein said patient breathing means is connected to an end of said valve means and said first means is connected to another end of said valve means so as to define a continuous path for gaseous flow through said internal cavity of said valve means from one end to the other end of said patient breathing means and said first means.

9. A ventilation study system according to claim 8 in which the valve means is positioned between said patient breathing means and said breathing bag means.

10. A ventilation study system according to claim 1 wherein said patient breathing means is connected to said first means which in turn is connected to said valve means so as to define a continuous path for gaseous flow from said internal cavity of said valve means to said patient breathing means.

11. A ventilation study system according to claim 1 in which the shearable polymeric capsule is comprised of a polymer selected from the group consisting of vinyl-vinylidene chloride, polyethylene-terephthalate and polysulfone.

12. In a ventilation study system for pulmonary function studies in patients, said system having an internal, gas-retaining volume and being adapted for operative connection to a patient's breathing process, the combination comprising:

a. a shearable polymeric capsule containing a gaseous radioisotope;

b. valve means comprised of a radiation shielding material having an internal cavity being adapted to be in operative communication with a patient's breathing process and holding said capsule, said cavity forming a portion of the gas-retaining volume of the system and said valve means further having a bore intersecting said cavity at an intermediate point of said capsule;

c. a rotatable valve plug comprised of a radiation shielding material positioned within the bore and having an opening concentric and normally aligned with the internal cavity of said valve means, said valve plug causing, upon rotation thereof, said capsule in the internal cavity of said valve means to be sheared, and thereby releasing the gaseous radioisotope; and d. breathing bag means defining a predetermined portion of the gas-retaining volume of the system being operatively connected to said valve means so as to be in communication with the internal cavity thereof, said breathing bag means being adapted to receive the patient's exhalation containing said gaseous radioisotope.

* * * * *